United States Patent [19]

Helioff et al.

[11] Patent Number: 5,066,481
[45] Date of Patent: Nov. 19, 1991

[54] MOUSSE HAIR COMPOSITION

[75] Inventors: Michael W. Helioff, Westfield; Krystyna Plochocka, Scotch Plains; Mohammed Tazi, Wayne, all of N.J.

[73] Assignee: ISP Investments Inc., Wilmington, Del.

[21] Appl. No.: 608,949

[22] Filed: Nov. 5, 1990

[51] Int. Cl.$^5$ .................................................. A61K 7/11
[52] U.S. Cl. .......................................... 424/47; 424/45; 424/71; 424/78; 424/DIG. 1
[58] Field of Search ...................... 424/45, DIG. 1, 47, 424/71, 78

[56] References Cited

U.S. PATENT DOCUMENTS

| 3,850,178 | 11/1974 | Schoenholz | 424/71 |
| 4,059,688 | 10/1977 | Rosenberg | 424/DIG. 1 |
| 4,348,380 | 9/1982 | Jacquet | 424/60 |
| 4,638,822 | 1/1987 | Grollier | 424/DIG. 1 |
| 4,897,262 | 1/1990 | Nandagiri | 424/DIG. 2 |
| 4,925,659 | 5/1990 | Grollier | 424/DIG. 1 |

Primary Examiner—Thurman K. Page
Assistant Examiner—Edward J. Webman
Attorney, Agent, or Firm—Walter Katz; Marilyn J. Maue; Joshua J. Ward

[57] ABSTRACT

The mousse hair composition of the invention comprises a resin provided by about 3–15% by weight of about a 20–50% alcoholic solution of the half-alkyl ester of a $C_1$–$C_5$ alkyl vinyl ether-maleic anhydride copolymer having a molecular weight of at least one million, which is about 5–90% neutralized, preferably with about 0.15–1.0% by weight of ammonium hydroxide, about 60–95% by weight of water, about 0.3–2.0% by weight of a surfactant, and about 0–30% by weight of added ethanol.

6 Claims, No Drawings

5,066,481

MOUSSE HAIR COMPOSITION

BACKGROUND OF THE INVENTION

1. Field of the Invention

This invention relates to a foamed hair product, and more particularly, to mousse hair compositions which provide a stable and expandable foam, a soft hold, and effective luster and shine for the hair of the user.

2. Description of the Prior Art

Mousse hairstyling products have become popular with the public. Such products are dispensed from an aerosol can as a pressure sensitive foam which is released upon the hair, typically after the hair is shampooed and towel dried. A mousse gives an appearance of penetration of the hair as the foam collapses and has ingredients that perform functions that are needed for the improved styling of hair. In particular, some of the purposes of these ingredients are to add body to the hair, thereby making it appear fuller on the head of the user, and to enhance the combability of the hair in order to make it more manageable. In a mousse, some of the collapsed foam may be designed to be combed out of the hair during the process of styling.

Mousses are distinguished from hairsprays or hair setting sprays which are typically used during the final step in holding the set of the hair. Such hairsprays tend to form a film, with flexibility provided by plasticizers that allow the hair to have some freedom of motion. Pressurized hair spray is generally a solution of film-producing resins in an alcohol solvent, together with an appropriate propellant, usually packaged in a tin plate steel can. When sprayed on the hair, the product forms droplets of resin, which, when dry, impart support and stiffening properties to the individual hair fibers, by forming junctions between adjacent or intersecting hair fibers and thereby yielding a rigid network.

The prior art in this field is represented by U.S. Pat. Nos. 4,240,450; 4,371,517; and 4,673,569.

SUMMARY OF THE INVENTION

The mousse hair composition of the invention comprises a resin provided by about 3–15% by weight of about a 20–50% alcoholic solution of the half-alkyl ester of a $C_1$–$C_5$ alkyl vinyl ether-maleic anhydride copolymer having a molecular weight of at least about one million, which is about 5–90% neutralized, preferably with about 0.15–1.0% by weight of ammonium hydroxide, about 60–95% water, about 0.3–2.0% of a surfactant, and about 0–30% of added ethanol.

DETAILED DESCRIPTION OF THE INVENTION

In accordance with the invention, the mousse hair composition includes a hair styling and body forming resin which is the means or half-alkyl ester of a high molecular weight $C_1$–$C_5$ alkyl vinyl ether-maleic anhydride copolymer. The copolymer is available commercially in powder form as Gantrez ® AN-169 (GAF Chemicals Corp.), which is the methyl vinyl ether-maleic anhydride copolymer having a molecular weight of about one million, or more. Suitable half-alkyl esters of this copolymer include the ethyl or butyl half-ester compounds. Solutions of such Gantrez ® AN-169 half-esters are prepared as about a 30–50% resin active solution in ethanol.

The composition of the mousse hair composition of the invention is given below.

MOUSSE HAIR COMPOSITION

| | Component | Concentration (% by wt.) | | |
|---|---|---|---|---|
| | | Suitable | Preferred | Optimum |
| A | Gantrez ® AN-169 (Half-Ester Solution) (30-50% active) | 3-15 | 5-10 | 5.8 |
| B | Water | 60-95 | 75-85 | 80.4 |
| C | $NH_4OH$ | 0.15-1.0 | 0.2-0.5 | 0.3 |
| D | Surfactant | 0.3-2.0 | 0.5-1.0 | 0.6 |
| E | Ethanol | 0-30 | 5-15 | 12.9 |
| | | | | 100.0 |

The water-based phase of the composition includes water as a solvent and a foam-forming chemical. The alcohol-based phase includes the hair styling and a body forming resin, a neutralizing agent and alcohol as a secondary solvent.

The foam-forming chemical is a non-ionic surfactant such as Emulphor ® ON-870 (Rhone-Poulenc Inc.), which is a polyethylene glycol ether of oleyl alcohol, PEG =20.

The method of manufacture of the mousse hair product of the invention comprises adding water and the neutralized ethanol solution of half-esterified Gantrez ® AN-169 into a stainless steel mixing tank and agitating at 45°° C. until dissolved. Then Emulphor ® ON-870 surfactant, (Rhone-Poulenc), polyethylene glycol ether of oleyl alcohol =PEG 20, is added and the contents are cooled to 40° C. A fragrance may be added at this point, if desired. After cooling to room temperature, the concentrate is pressurized with a suitable amount of propellant.

Suitably, the aerosol mousse product comprises about 80–95% by weight of the mousse hair composition and about 5–20% by weight of propellant. In the preferred composition, the propellant is a mixture of 70% propane and 30% isobutane.

In use, the aerosol mousse provides a stable and expandable foam, a soft hold, an excellent bubble distribution pattern, and effective luster and shine on the hair of the user. In addition, the product is stable in aluminum or tin plate steel aerosol containers.

In comparative tests with a similar aerosol mousse formulation containing a 50% active ethanol solution of Gantrez ® ES-225 (GAF Chemicals Corporation) in place of the active resin solution of this invention, less advantageous hair properties were obtained.

While the invention has been described with particular reference to certain embodiments thereof, it will be understood that changes and modifications may be made which are within the skill of the art. Accordingly, it is intended to be bound only by the following claims, in which:

What is claimed is:

1. A mousse hair composition for aerosol use consisting essentially of a resin provided by about 3–15% by weight of about a 20–50% resin active alcoholic solution of the monoester of a $C_1$–$C_5$ alkyl vinyl ether-maleic anhydride copolymer having a molecular weight of at least about one million, which is about 5–90% neutralized, about 60–95% by weight of water, about 0.3–2.0% of surfactant and about 0—30% of added ethanol.

2. A composition according to claim 1 wherein said half-alkyl ester is the monoethyl or monobutyl ester, and the alkyl vinyl ether is the methyl vinyl ether.

3. A composition according to claim 1 wherein said copolymer is neutralized with about 0.15-1.0% by weight of ammonium hydroxide.

4. A composition according to claim 2 which comprises about 5-10% by weight of said resin active alcoholic solution, about 75-85% by weight of water, about 0.2-0.5% by weight of ammonium hydroxide, about 0.5-1.0% by weight of a surfactant, and about 5-15% by weight of added ethanol.

5. A composition according to claim 2 comprising about 5.8% by weight of said resin active alcohol solution, about 80.4% by weight of water, about 0.3% by weight of ammonium hydroxide, about 0.6% by weight of surfactant, and about 12.9% by weight of added ethanol.

6. An aerosol mousse hair product comprising about 80-95% by weight of the mousse hair composition of claim 1 and about 5-20% by weight of a propellant.

* * * * *